(12) United States Patent
Li et al.

(10) Patent No.: US 11,832,957 B2
(45) Date of Patent: Dec. 5, 2023

(54) IMPEDANCE-TYPE CHIP FOR REAL-TIME SENSING SWEAT PRESSURE AND METHOD THEREOF

(71) Applicant: National Yang Ming Chiao Tung University, Hsinchu (TW)

(72) Inventors: Bor-Ran Li, Hsinchu (TW); Pei-Heng Lin, Hsinchu (TW); Wei-Lung Chang, Hsinchu (TW); Sian-Chen Sheu, Hsinchu (TW)

(73) Assignee: National Yang Ming Chiao Tung University, Hsinchu (TW)

( * ) Notice: Subject to any disclaimer, the term of this patent is extended or adjusted under 35 U.S.C. 154(b) by 288 days.

(21) Appl. No.: 17/212,098

(22) Filed: Mar. 25, 2021

(65) Prior Publication Data

US 2022/0304618 A1 Sep. 29, 2022

(30) Foreign Application Priority Data

Feb. 24, 2020 (TW) .................. 109105928

(51) Int. Cl.
*A61B 5/00* (2006.01)
*A61B 5/0531* (2021.01)
(Continued)

(52) U.S. Cl.
CPC .............. *A61B 5/4266* (2013.01); *A61B 5/01* (2013.01); *A61B 5/0531* (2013.01); *G01N 27/028* (2013.01); *G01N 33/48707* (2013.01)

(58) Field of Classification Search
CPC ....... A61B 5/4266; A61B 5/01; A61B 5/0531; G01N 27/028; G01N 33/48707
See application file for complete search history.

(56) References Cited

U.S. PATENT DOCUMENTS

| 8,440,093 | B1* | 5/2013 | Nassef ............... | G01N 15/1031 |
| | | | | 216/84 |
| 2004/0000713 | A1* | 1/2004 | Yamashita ............ | H10N 10/17 |
| | | | | 374/E7.035 |

(Continued)

OTHER PUBLICATIONS

Azar Alizadeh et al., A Wearable Patch for Continuous Monitoring of Sweat Electrolytes During Exertion, Lab Chip, Jul. 31, 2018, pp. 2632-2641, vol. 18, The Royal Society of Chemistry.

(Continued)

*Primary Examiner* — Daniel L Cerioni (57) ABSTRACT

An impedance-type chip for real-time sensing sweat pressure, a micro-control system, and method thereof are provided for monitoring a physiological state of a subject. The impedance-type chip includes a substrate, a pair of comb-shaped electrodes, a first double-layered junction plate, a microfluidic channel plate, a second double-layered junction plate, and a sealing plate. Each the comb-shaped electrodes has a plurality of sub-electrodes and is disposed on the substrate to provide different impedance values. The first double-layered junction plate is disposed on the substrate, the microfluidic channel plate is disposed on the first double-layered junction plates, and the second double-layered junction plate is disposed on the microfluidic channel plate, wherein the first double-layered junction plate, the microfluidic channel plate, and the second double-layered junction plate have a microfluidic channel with a cavity. The sealing plate is disposed on the second double-layered junction plate to seal the microfluidic channel.

8 Claims, 11 Drawing Sheets

(51) Int. Cl.
*G01N 33/487* (2006.01)
*G01N 27/02* (2006.01)
*A61B 5/01* (2006.01)

(56) References Cited

U.S. PATENT DOCUMENTS

2019/0094178 A1* 3/2019 Delamarche ........ B01L 3/50273
2020/0337641 A1* 10/2020 Wang ................... A61B 5/1486
2020/0397315 A1* 12/2020 Raj ........................ A61B 5/486

OTHER PUBLICATIONS

Nimisha Srivastava et al., Microfluidic Pressure Sensing Using Trapped Air Compression, Lab Chip, May 2007, pp. 633-637, vol. 7, Issue 5, The Royal Society of Chemistry.
Ashlesha Bhide et al., Simultaneous Lancet-free Monitoring of Alcohol and Glucose from Low-volumes of Perspired Human Sweat, Scientific Reports, Apr. 25, 2018, pp. 1-11, vol. 8, Issue 6507.
Jungil Choi et al., Soft, Skin-mounted Microfluidic Systems for Measuring Secretory Fluidic Pressures Generated at the Surface of the Skin by Eccrine Sweat Glands, Lab Chip, Jun. 16, 2017, cover page and pp. 2572-2580, vol. 17, The Royal Society of Chemistry.
Yuksel Temiz et al., Sub-nanoliter, Real-time Flow Monitoring in Microfluidic Chips Using a Portable Device and Smartphone, Scientific Reports, Jul. 13, 2018, pp. 1-11, vol. 8, Issue 10603.
Z. Sonner et al., The Microfluidics of the Eccrine Sweat Gland, Including Biomarker Partitioning, Transport, and Biosensing Implications, Biomicrofluidics, May 15, 2015, pp. 1-19, vol. 9, Issue 031301.

\* cited by examiner

IMPEDANCE-TYPE CHIP FOR REAL-TIME SENSING SWEAT PRESSURE AND METHOD THEREOF

CROSS REFERENCE TO RELATED APPLICATIONS

The present application claims the benefit of Taiwanese Patent Application No. 109105928 filed on Feb. 24, 2020, the contents of which are incorporated herein by reference in their entirety.

FIELD OF TECHNOLOGY

The invention relates to an impedance-type chip for real-time sensing sweat pressure, a micro-control system and a method thereof, particularly, an impedance-type chip having a pair of comb-shaped electrodes and a microfluidic channel with a sweat inflow hole and a cavity connected with the microfluidic channel.

BACKGROUND

The physiological function of sweating is to regulate body temperature. The current physiological state, such as temperature regulation, metabolism, or dehydration, with some calculation is possible to be obtained according to the immediate state of sweating. Therefore, detecting the state of perspiration and analyzing the composition of sweat can be used as an important indicator to determine the physiological states. However, as for detecting the amount of perspiration, efficient, real-time and digital analysis is still a challenge.

In recent years, among many methods for analyzing skin surface fluids, detection of sweat or its components by electrical signals is the most concerned analysis method. Using electrical signals to detect the sweat and/or its composition is mainly to detect sweat secretion based on the capacitance, current, or impedance. Electrochemical methods are alternatively used to analyze signals in sweat, such as ions, pH value, or glucose concentration. Further, method of analyzing the sweat via electrical signals is precise, and thus can be widely applied to wearable devices.

SUMMARY

An aspect of the invention is to provide an impedance-type chip having a cavity and a microfluidic channel with a sweat inflow hole, and detecting a sweat pressure when sweat flows into the microfluidic channel. The impedance-type chip for real-time sensing sweat pressure comprises a pair of comb-shaped electrodes, a microfluidic channel with a sweat inflow hole, and a cavity connected with the microfluidic channel. Another aspect of the invention is to provide an impedance-type chip that can measure the sweat with high efficiency, high accuracy, and in real-time, as well as have the characteristics of low cost and reusability. According to an embodiment of the invention, the cavity is connected to the microfluidic channel with the sweat inflow hole, and the sweat pressure is generated when the sweat flows into the microfluidic channel. According to another embodiment of the invention, the impedance-type chip is capable of measuring the sweat pressure in the microfluidic channel resulted from the characteristics of comb-shaped electrodes each having a plurality of sub-electrodes to standardize and digitalize the sweat pressure of the sweat secreted by sweat glands in order to show a subject's current status.

Specifically, according to an embodiment of the invention, an impedance-type chip for real-time sensing sweat pressure is provided and applied to instantly detect the amount of perspiration and the state of sweat secretion in a subject's daily life or exercise. The impedance-type chip comprises a substrate, a pair of comb-shaped electrodes, a first double-layered junction plate, a microfluidic channel plate, a second double-layered junction plate, and a sealing plate. The substrate is used as a stable bearing panel. The pair of the comb-shaped electrodes has plural pairs of oppositely-disposed sub-electrodes, on the substrate, to provide different impedance values. The first double-layered junction plate is disposed on the substrate and the comb-shaped electrodes. The microfluidic channel plate is disposed on the first double-layered junction plates. The second double-layered junction plate is disposed on the microfluidic channel plate. The first double-layered junction plate, the microfluidic channel plate, and the second double-layered junction plate define a microfluidic channel overlapping on the comb-shaped electrodes and a cavity connected with the microfluidic channel, and the microfluidic channel has a sweat inflow hole. The sealing plate is disposed on the second double-layered junction plate to seal the microfluidic channel and the cavity, wherein the sealing plate has a sweat inflow hole disposed on the sweat inflow hole of the microfluidic channel.

According to another embodiment of the invention, each pair of the oppositely-disposed sub-electrodes has a gap of 1-1.4 mm.

According to yet another embodiment of the invention, the impedance-type chip further comprises a sweat monitor configured to measure a sweat resistance value between the comb-shaped electrodes and a total number of the sub-electrodes contacted by sweat.

According to still another embodiment of the invention, the impedance-type chip further comprises a temperature sensor configured to measure a body temperature of the subject.

According to still another embodiment of the invention, the impedance-type chip further comprises a communicating circuit configured to output the sweat resistance value, the total number of the sub-electrodes contacted by the sweat, and the body temperature.

According to another embodiment of the invention, a micro-control system for controlling the impedance-type chip is further provided, in addition to the impedance-type chip. The micro-control system may be applied to instantly detect the amount of perspiration and the state of sweat secretion in a subject's daily life or exercise. The micro-control system comprises a pulsed voltage output module, a signal correction module, an equivalent resistance and correction module, and a sweat pressure conversion module. The pulsed voltage output module is configured to regularly output a pulsed voltage to the pair of the comb-shaped electrodes in real time. The signal correction module is configured to output an inverse pulsed voltage, opposite to the pulsed voltage, to the pair of the comb-shaped electrodes of the impedance-type chip above in real time. The equivalent resistance and correction module is configured to receive the sweat resistance value, the total number of the sub-electrodes contacted by the sweat and the body temperature of the subject output by the communicating circuit, and output a calibrated resistance value and the body temperature. The sweat pressure conversion module is configured to receive and convert the calibrated resistance value and the body temperature to a sweat pressure value.

According to another embodiment of the invention, the micro-control system further comprises a bluetooth module configured to receive and output the sweat pressure value to an external device.

According to still another embodiment of the invention, the equivalent resistance and correction module further comprises an equivalent circuit configured to correct an effect to the sweat resistance value caused by a sweat ion concentration and a sweat pH value via a normalized curve based on the sweat resistance value and the total number of sub-electrodes contacted by the sweat, as well as calculate the calibrated resistance value.

Furthermore, according to still another embodiment of the invention, a method for real-time sensing sweat pressure by using the impedance-type chip and the micro-control system is provided. The method may be applied to instantly detect the amount of perspiration and the state of sweat secretion in a subject's daily life or exercise. The method comprises the following steps. The pulsed voltage is applied to the pair of the comb-shaped electrodes in real time to contact sweat. The sweat resistance value and the total number of sub-electrodes contacted by the sweat are measured via the sweat monitor. The body temperature is measured by the temperature sensor. The inverse pulsed voltage, opposite to the pulsed voltage, is applied to the comb-shaped electrodes in real time for avoiding electrochemical reactions between the comb-shaped electrodes and the sweat. The calibrated resistance value is calculated based on the sweat resistance value and the total number of the sub-electrodes contacted by the sweat via the equivalent resistance and correction module. The calibrated resistance value and the body temperature are converted to the sweat pressure value.

According to another embodiment of the invention, the method further comprises the following steps. An effect to the sweat resistance value caused by a sweat ion concentration and a sweat pH value is corrected via a normalized curve based on the sweat resistance value and the total number of sub-electrodes contacted by the sweat to obtain the calibrated resistance value. The calibrated resistance value is output.

Accordingly, an impedance-type chip for real-time sensing sweat pressure having a microfluidic channel with a sweat inflow hole and a cavity connected with the microfluidic channel is provided. Sweat may cause the sweat pressure when the sweat flows into the microfluidic channel. The sweat pressure can be standardized and digitalized by using the characteristics of the pair of the comb-shaped electrodes having plural pairs of oppositely-disposed sub-electrodes to provide different impedance values. Moreover, because the sweat generated by sweat glands may still be reabsorbed by human skin, the sweat pressure may thus be continuously measured for a long time.

BRIEF DESCRIPTION OF THE DRAWINGS

The following detailed description in conjunction with drawings will enable those ordinarily skilled in the art to make or use the invention.

DETAILED DESCRIPTION

The following description is illustrated with drawings for technical features, contents and advantages according to some embodiments of the invention. The attached drawings are only used for illustrative purposes to support the description, and the embodiments of the invention may not be interpreted and limited to the scale and configurations shown in the attached drawings.

Accordingly, an impedance-type chip for real-time sensing sweat pressure, a micro-control system and a method thereof are provided. When analyzing physiological state of a subject, there are many indicators that can be referenced, such as heart rhythm, body temperature, blood pressure, etc. However, as for analyzing the composition of secretion on a body surface, there is no else indicator that can be digitized and meanwhile statistically analyzed except for a direct analysis on the composition of secretion. Structurally, the impedance-type chip has a microfluidic channel with a sweat inflow hole, a pair of comb-shaped electrodes overlapping the microfluidic channel, and a cavity connected with the microfluidic channel. The pair of comb-shaped electrodes of the impedance-type chip have plural pairs of oppositely-disposed sub-electrodes, on a substrate of the impedance-type chip, to provide different impedance values. Therefore, sweat may cause the sweat pressure after the sweat flows into the microfluidic channel. Then, the comb-shaped electrodes are used to digitize the distance of sweat inflow. As the displacement of the sweat in the microfluidic channel increases, the number of the contacted comb-shaped electrodes increases and the measured resistance value thereof decreases, which may thus be converted into a sweat pressure value. The sweat pressure value may be used as an indicator in the subsequent analysis of the secretion on the body surface or the modulation state of the body temperature.

Figure 1:
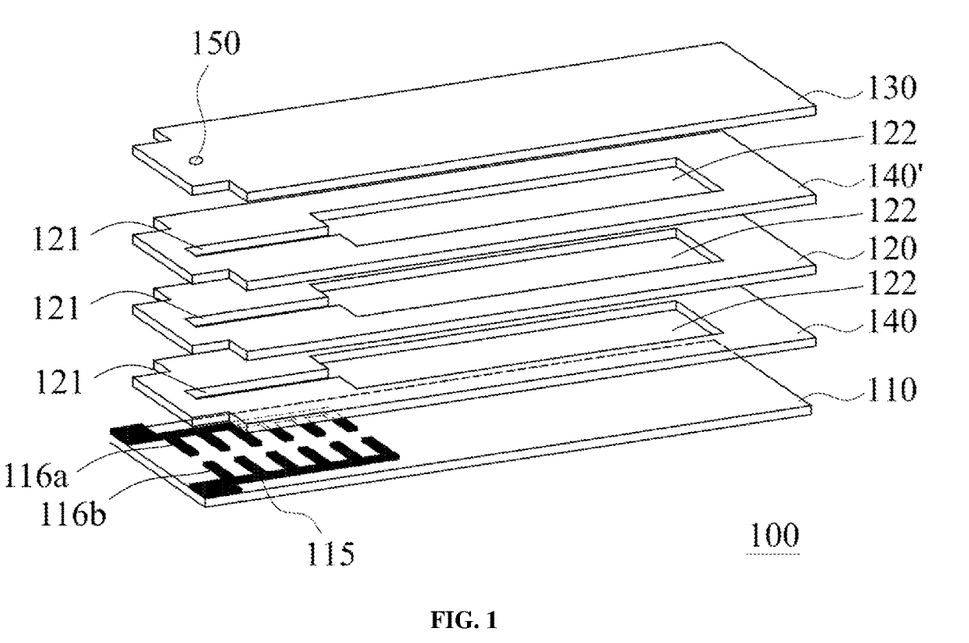
FIG. 1 is a diagram of an impedance-type chip for real-time sensing sweat pressure according to an embodiment of the invention.

In order to more clearly illustrate the implementation and technical features according to some embodiments of the invention, please refer to FIG. 1. FIG. 1 is a diagram of an impedance-type chip for real-time sensing sweat pressure according to an embodiment of the invention. In FIG. 1, an impedance-type chip 100 is provided for real-time sensing sweat pressure to monitor and record a physiological state of a subject. The impedance-type chip 100 comprises a substrate 110, a pair of comb-shaped electrodes 115, a first double-layered junction plate 140, a microfluidic channel plate 120, a second double-layered junction plate 140', and a sealing plate 130.

The impedance-type chip 100 is further described as below. The comb-shaped electrodes 115 having plural pairs of oppositely-disposed sub-electrodes 116a, 116b are printed on one end of the substrate 110 to provide different impedance values. According to another embodiment of the invention, each pair of the oppositely-disposed sub-electrodes 116a, 116b has a gap of 1-1.4 mm. The first double-layered junction plate 140 is disposed on the substrate 110 and the comb-shaped electrodes 115. The microfluidic channel plate 120 is disposed on the first double-layered junction plates 140. The second double-layered junction plate 140' is disposed on the microfluidic channel plate 120. The first double-layered junction plate 140, the microfluidic channel plate 120, and the second double-layered junction plate 140' form a microfluidic channel 121 with a sweat inflow hole 150, and a cavity 122 connected with the microfluidic channel. The microfluidic channel 121 overlaps on the comb-shaped electrodes 115. More specifically, the plural pairs of oppositely-disposed sub-electrodes 116a, 116b of the pair of comb-shaped electrodes 115 disposed on two sides of the microfluidic channel 121. The sealing plate 130 is disposed on the second double-layered junction plate 140' to seal the microfluidic channel 121 and the cavity 122, and the sealing plate 130 has a sweat inflow hole 150 to be the single entrance of the microfluidic channel 121.

Figure 2:
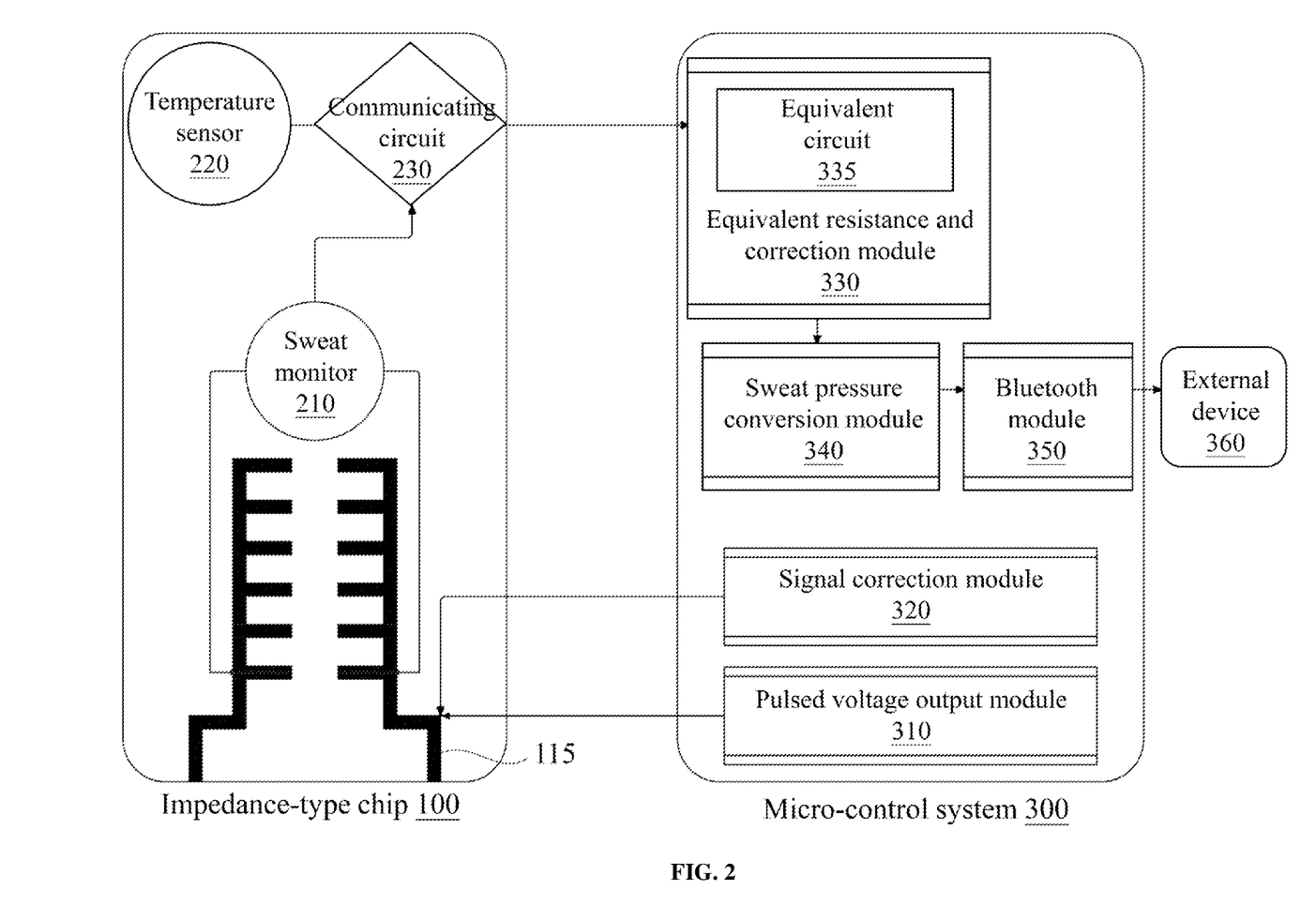
FIG. 2 is a diagram illustrating the connection of the impedance-type chip and a micro-control system according to an embodiment of the invention.

FIG. 2 is a diagram illustrating the connection of the impedance-type chip and a micro-control system according to an embodiment of the invention. In FIG. 2, the impedance-type chip for real-time sensing sweat pressure 100 further comprises a sweat monitor 210, a temperature sensor 220, and a communicating circuit 230.

The impedance-type chip 100 for real-time sensing sweat pressure is further described as below. The sweat monitor 210 is configured to measure a sweat resistance value and a total number of the sub-electrodes 116a, 116b contacted by sweat after the sweat flows into the microfluidic channel 121. The temperature sensor 220 is configured to measure a body temperature of the subject. The communicating circuit 230 is configured to output the sweat resistance value, the total number of sub-electrodes 116a, 116b contacted by the sweat, and the body temperature.

According to another embodiment of the invention, a micro-control system 300 for controlling the impedance-type chip 100 to monitor and record a physiological state of the subject is provided in FIG. 2. The micro-control system 300 further comprises a pulsed voltage output module 310, a signal correction module 320, an equivalent resistance and correction module 330, and a sweat pressure conversion module 340.

The micro-control system 300 is further described as below. The micro-control system 300 further comprises a bluetooth module 350 and an external device 360. The bluetooth module 350 is configured to receive and output the sweat pressure value to the external device 360. The external device 360 is any system or device, capable of computing data and logic judgment, comprising desktop computers, notebooks, and smart phones.

The equivalent resistance and correction module 330 further comprises an equivalent circuit 335.

The pulsed voltage output module 310 is configured to regularly output a pulsed voltage to the pair of the comb-shaped electrodes 115 in real time. The signal correction module 320 is configured to regularly output an inverse pulsed voltage, opposite to the pulsed voltage, to the pair of the comb-shaped electrodes 115 in real time. Further, the pulsed voltage and the inverse pulsed voltage may be generated in every specified time interval, such as every hour, every half of a day, or every day. The equivalent resistance and correction module 330 is configured to receive the sweat resistance value, the total number of the sub-electrodes 116a, 116b contacted by the sweat and the body temperature of the subject output by the communicating circuit 230, and output a calibrated resistance value and the body temperature. In the calculation, a normalized curve is used to correct the effect of a sweat ion concentration and a sweat pH value on the sweat resistance value to obtain the calibrated resistance value, and then the body temperature and the calibrated resistance value are output. The sweat pressure conversion module 340 is configured to receive and convert the calibrated resistance value and the body temperature to a sweat pressure value, and further output the sweat pressure value to the bluetooth module 350 and then the external device 360.

Figure 3:
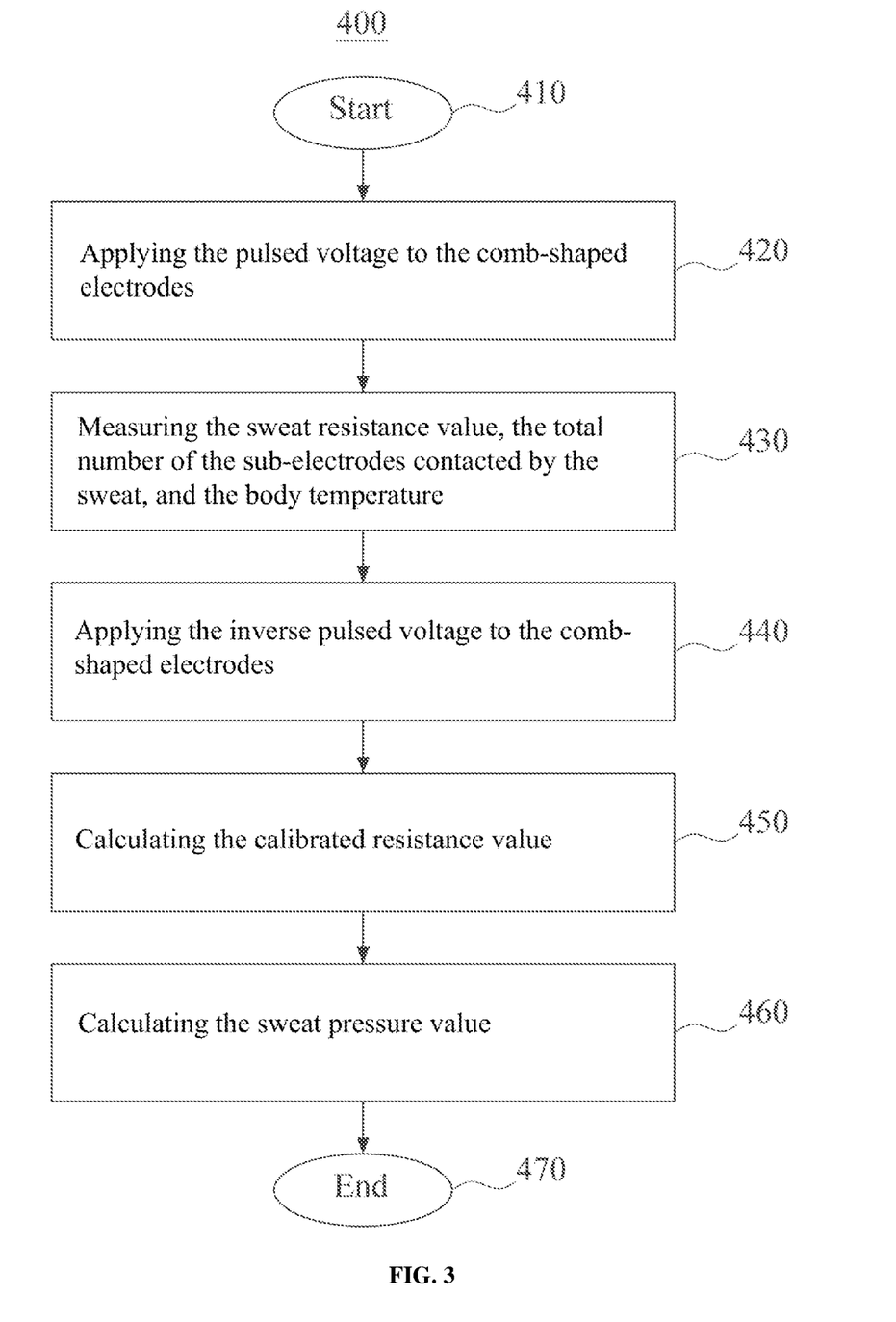
FIG. 3 is a flowchart of a method for real-time sensing sweat pressure by using the impedance-type chip and the micro-control system according to an embodiment of the invention.

FIG. 3 is a flowchart 400 of a method for real-time sensing sweat pressure by using the impedance-type chip and the micro-control system according to an embodiment of the invention. In FIG. 3, the method for real-time sensing sweat pressure by using the impedance-type chip and the micro-control system comprises the following steps.

First, the method is started from step 410. Next, in step 420, sweat flows into the microfluidic channel 121 through the sweat inflow hole 150, and the pulsed voltage is regularly applied to the comb-shaped electrode 115 in real time by using the pulsed voltage output module 310, wherein the pulsed voltage may pass through the sub-electrodes 116a, 116b contacted by the sweat.

Next, in step 430, the sweat resistance value and the total number of the sub-electrodes 116a, 116b contacted by the sweat are measured by using the sweat monitor 210. The body temperature is measured by using the temperature sensor 220. The sweat resistance value, the total number of the sub-electrodes 116a, 116b contacted by the sweat, and the body temperature are output by using the communicating circuit 230.

In step 440, the inverse pulsed voltage, opposite to the pulsed voltage, to the comb-shaped electrodes 115 in real time is applied by the signal correction module 320 for avoiding electrochemical reactions between the comb-shaped electrodes 115 and the sweat.

In step 450, the sweat resistance value, the total number of the sub-electrodes 116a, 116b contacted by the sweat, and the body temperature output by the communicating circuit 230 are received by the equivalent resistance and correction module 330. The sweat resistance value and the total number of the sub-electrodes 116a, 116b contacted by the sweat are further used by the equivalent circuit 335 to correct an effect caused by the sweat ion concentration and the sweat pH value via the normalized curve, as well as to calculate the calibrated resistance value to output the calibrated resistance value and the body temperature.

In step 460, the calibrated resistance value and the body temperature are received and converted to the sweat pressure by using the sweat pressure conversion module 340. The sweat pressure is then output to the bluetooth module 350 and then the external device 360.

Some examples are provided as below to show some advantages according to the embodiments of the invention, such as real-time response, and continuous non-invasive measurement, etc. The embodiments of the invention may be further combined with digital processing and wireless transmission to obtain the improved sensitivity, accuracy, and convenience of the impedance-type chip.

Figure 4:
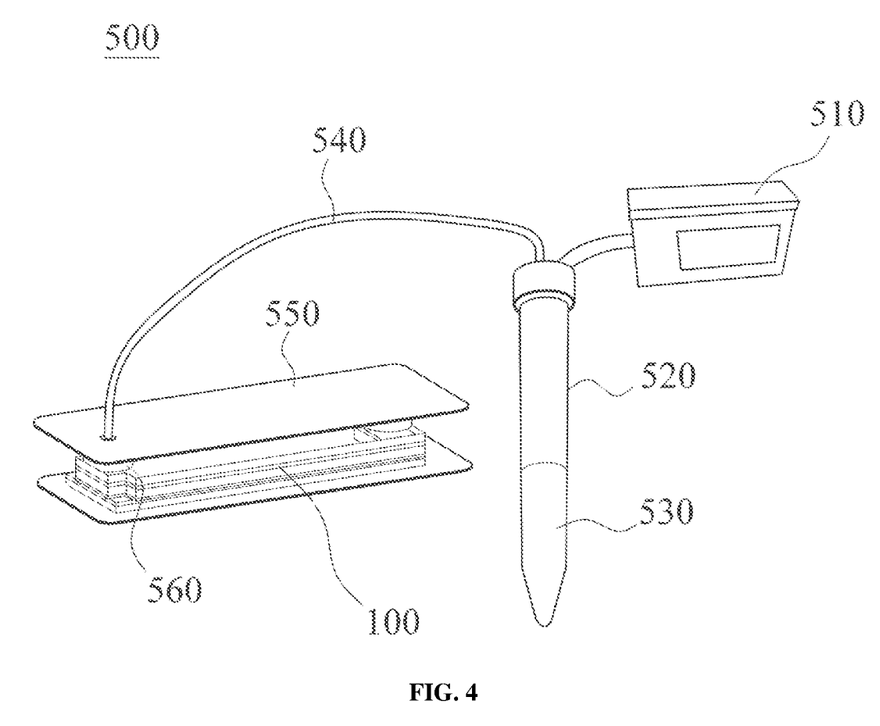
FIG. 4 is a schematic diagram of an experimental setup according to an embodiment of the invention.

FIG. 4 is a schematic diagram of an experimental setup according to an embodiment of the invention. In FIG. 4, an experimental device 500 was used to simulate the condition of the sweat secreted by the sweat glands and then flowing into the microfluidic channel 121 of the embodiment of the invention. The impedance-type chip 100 for real-time sensing sweat pressure in the experimental device 500 was formed by three layers of polyethylene terephthalate (PET) bonded together. In the experiments, artificial sweat 530 of different sodium ion concentration and pH value was prepared, and the artificial sweat 530 was then stored in a centrifuge tube 520. The centrifuge tube 520 was connected to a polydimethylsiloxane (PDMS) cylinder 560 by using a Teflon tube 540 to input the artificial sweat 530 to the microfluidic channel 121. Additionally, an input pressure of the artificial sweat 530 might be modified by using a pressure pump 510.

Figure 5:
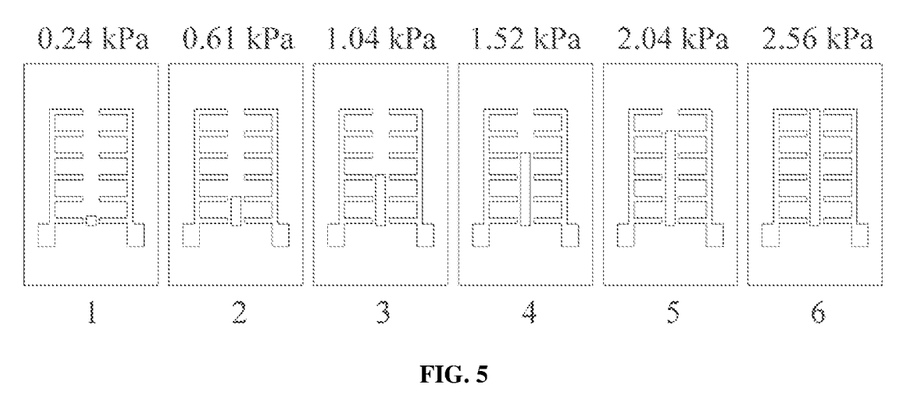
FIG. 5 is a schematic diagram based on an actual operating status of a microfluidic channel according to an embodiment of the invention.

FIG. 5 is a schematic diagram based on an actual operating status of a microfluidic channel according to an embodiment of the invention. In FIG. 5, the displacement of the artificial sweat 530 in the microfluidic channel 121 was increased as a result of increasing the input pressure of the artificial sweat 530 by using the pressure pump 510. Each of the sweat resistance values was respectively monitored by the six pairs of the sub-electrodes 116a, 116b. The measured input pressures in FIG. 5 were respectively 0.24 kPa, 0.61 kPa, 1.04 kPa, 1.52 kPa, 2.04 kPa, and 2.56 kPa, for example.

Figure 6:
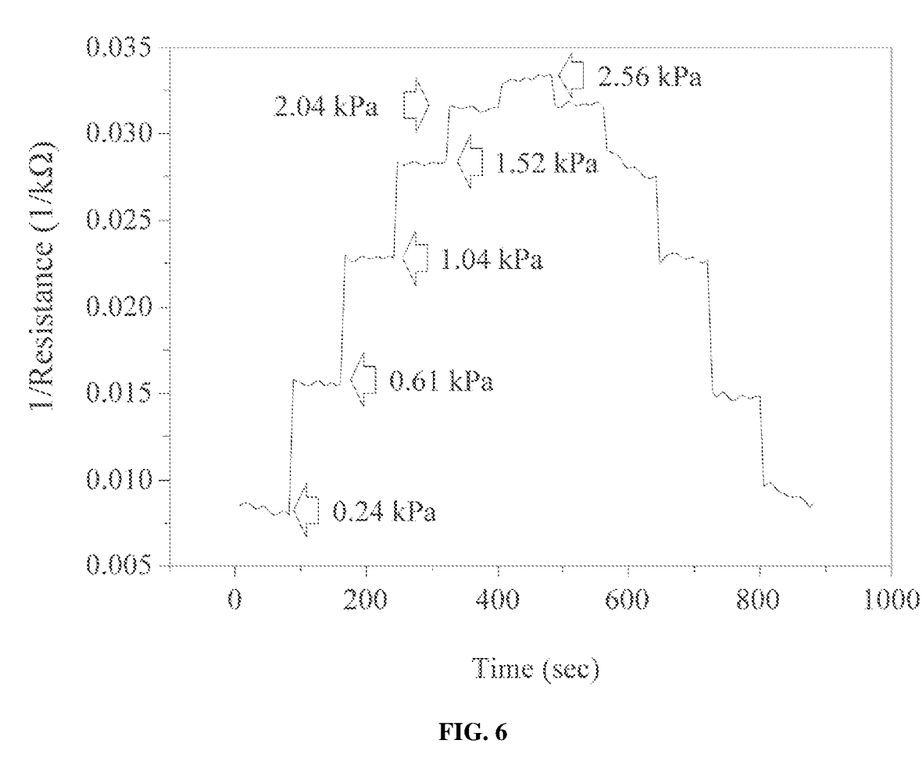
FIG. 6 is a diagram illustrating the relationship between the measured sweat resistance values and the input pressure of the impedance-type chip according to an embodiment of the invention.

FIG. 6 is a diagram illustrating the relationship between the measured sweat resistance values and the input pressure of the impedance-type chip according to an embodiment of the invention. The pressure pump 510 was used here to control the advancing of the artificial sweat 530 in the microfluidic channel 121. The micro-control system 300 then output the sensed results. A diagram of the input pressure, corresponding to the number of the sub-electrodes 116a, 116b contacted by the artificial sweat 530, and the measured resistance value vs. time are plotted to further prove that the embodiment of the invention might be used for real-time sensing sweat pressure. In FIG. 6, the data showed that the measured resistance values might be decreased when the pair number of the sub-electrodes 116a, 116b contacted by the artificial sweat 530 in the microfluidic channel 121 was increased.

Figure 7:
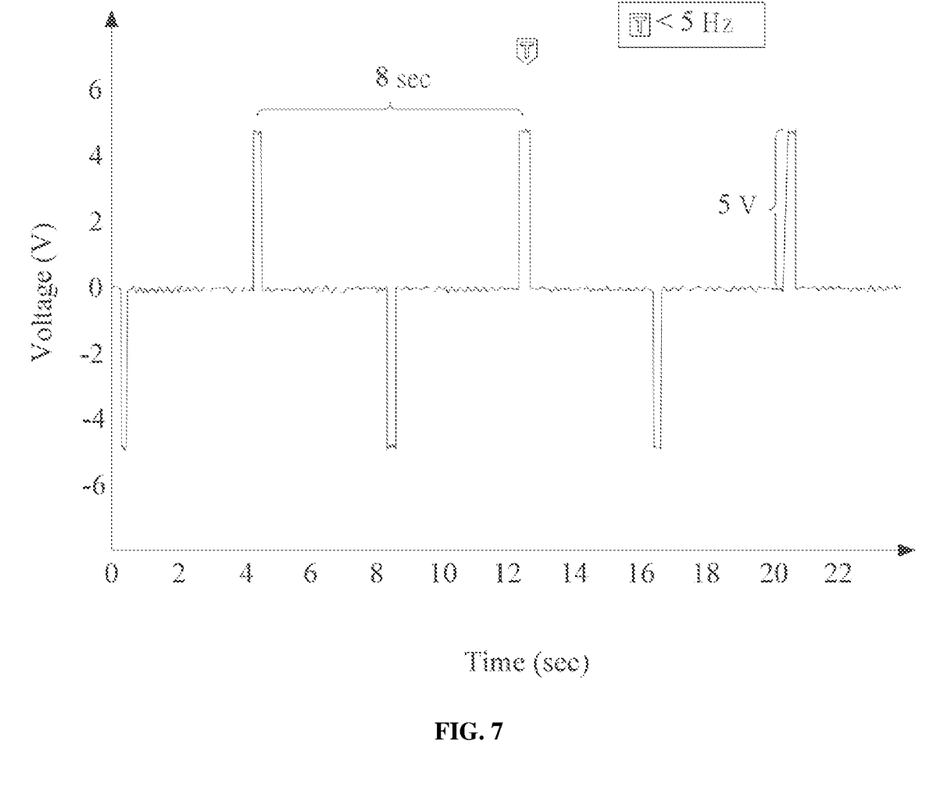
FIG. 7 is an output voltage diagram illustrating the pulsed voltage and the inverse pulsed voltage according to an embodiment of the invention.

FIG. 7 is an output voltage diagram illustrating the pulsed voltage and the inverse pulsed voltage according to an embodiment of the invention. In FIG. 7, an Arduino micro-control system was used as the micro-control system 300 according to the embodiment of the invention. A 5 V pulsed voltage and a 5 V inverse pulsed voltage with a specific frequency (8 seconds was used here as a period) were respectively applied on each pair of the sub-electrodes 116a, 116b to replace a DC voltage so that the resistance values might be measured. By this way, the electrochemical reaction between the sub-electrodes 116a, 116b and the electrolyte in the artificial sweat 530 was then reduced and avoided.

Figure 12:
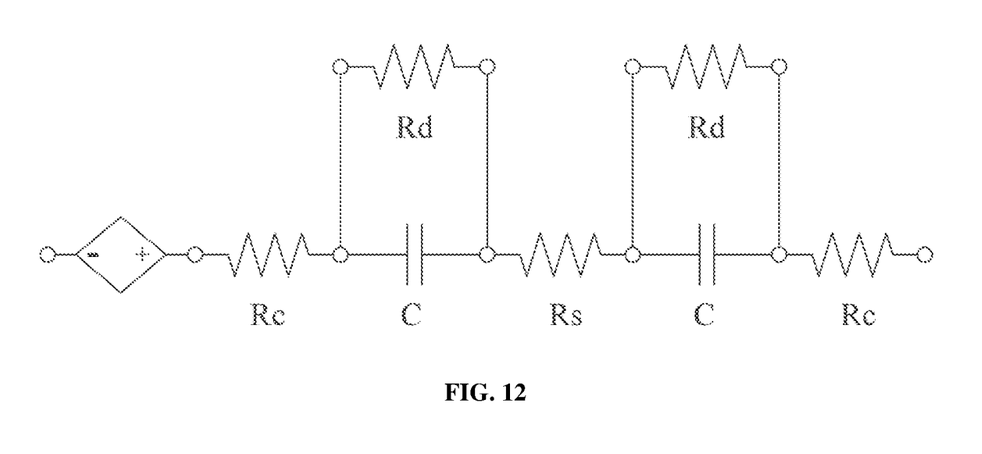
FIG. 12 is an equivalent circuit diagram according to an embodiment of the invention.

FIG. 12 is an equivalent circuit diagram according to an embodiment of the invention. The equivalent resistance conversion equation of the equivalent circuit 335 in FIG. 12 is as the following equation (1), wherein $E_h$ is the half-cell potential, $R_c$ is the resistance of electrode, $R_d$ is the resistance of double-layered junction plate, $R_s$ is the resistance of solution, and n is the total number of sub-electrodes 116a, 116b of the comb-shaped electrodes 115.

$$R = \frac{E_h}{I} + \frac{2R_c + 2R_d + R_s}{n} \qquad \text{equation (1)}$$

Figure 8:
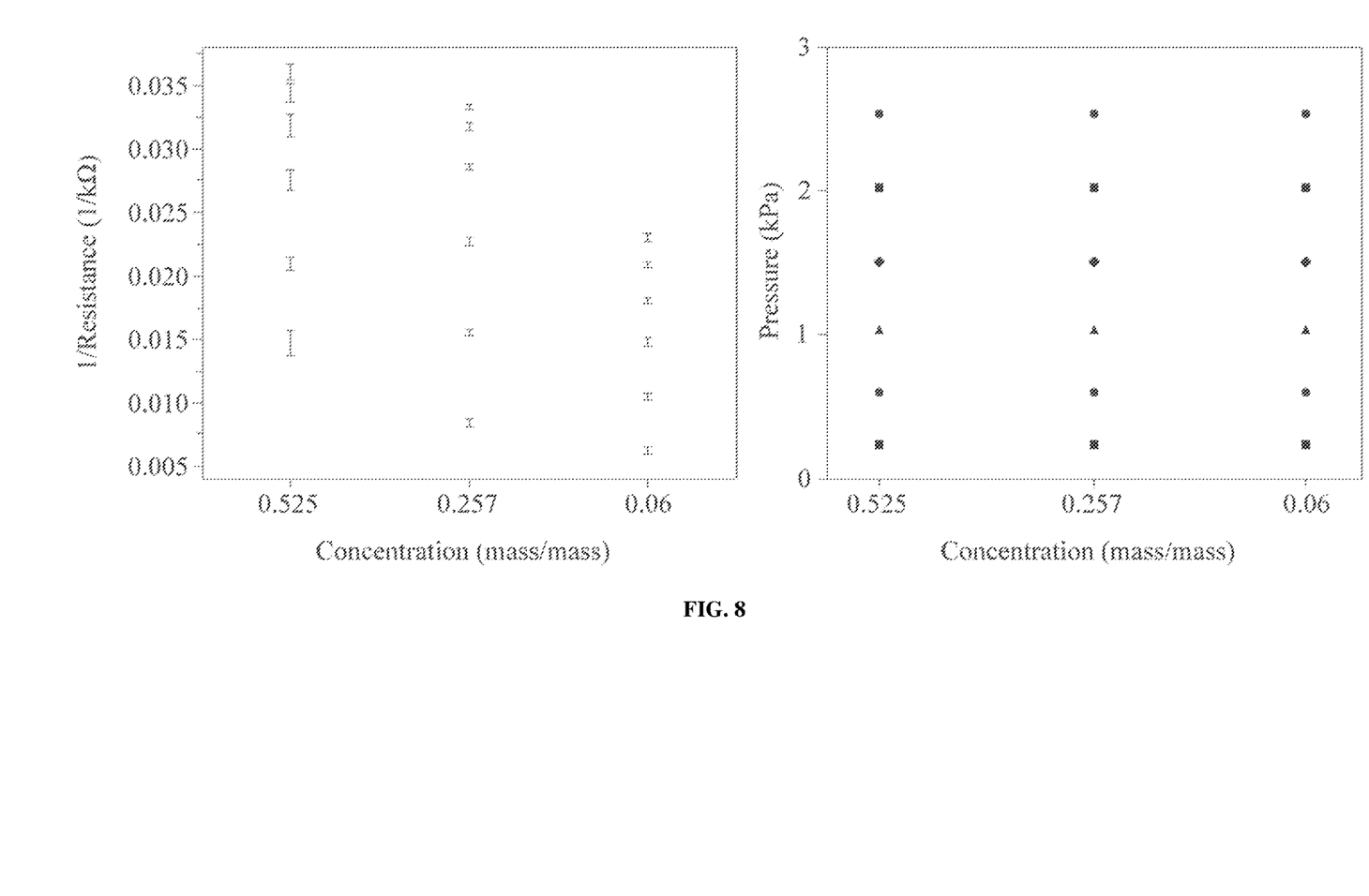
FIG. 8 is a diagram illustrating the measurement difference of the ion concentration and the calibration thereof according to an embodiment of the invention.

FIG. 8 is a diagram illustrating the measurement difference of the ion concentration and the calibration thereof according to an embodiment of the invention. In FIGS. 8 and 12, different measurement results according to the embodiment of the invention were obtained for the different sweat ion concentration, so the resistance value of the sweat advanced to the first pair of the sub-electrodes 116a, 116b by using the Arduino micro-control system was then measured. Further, the calculation of the equivalent circuit 335 as above was used to eliminate the effect caused by the ion concentration and the calibration curve of the corresponding ion concentration was then directly introduced.

Figure 9:
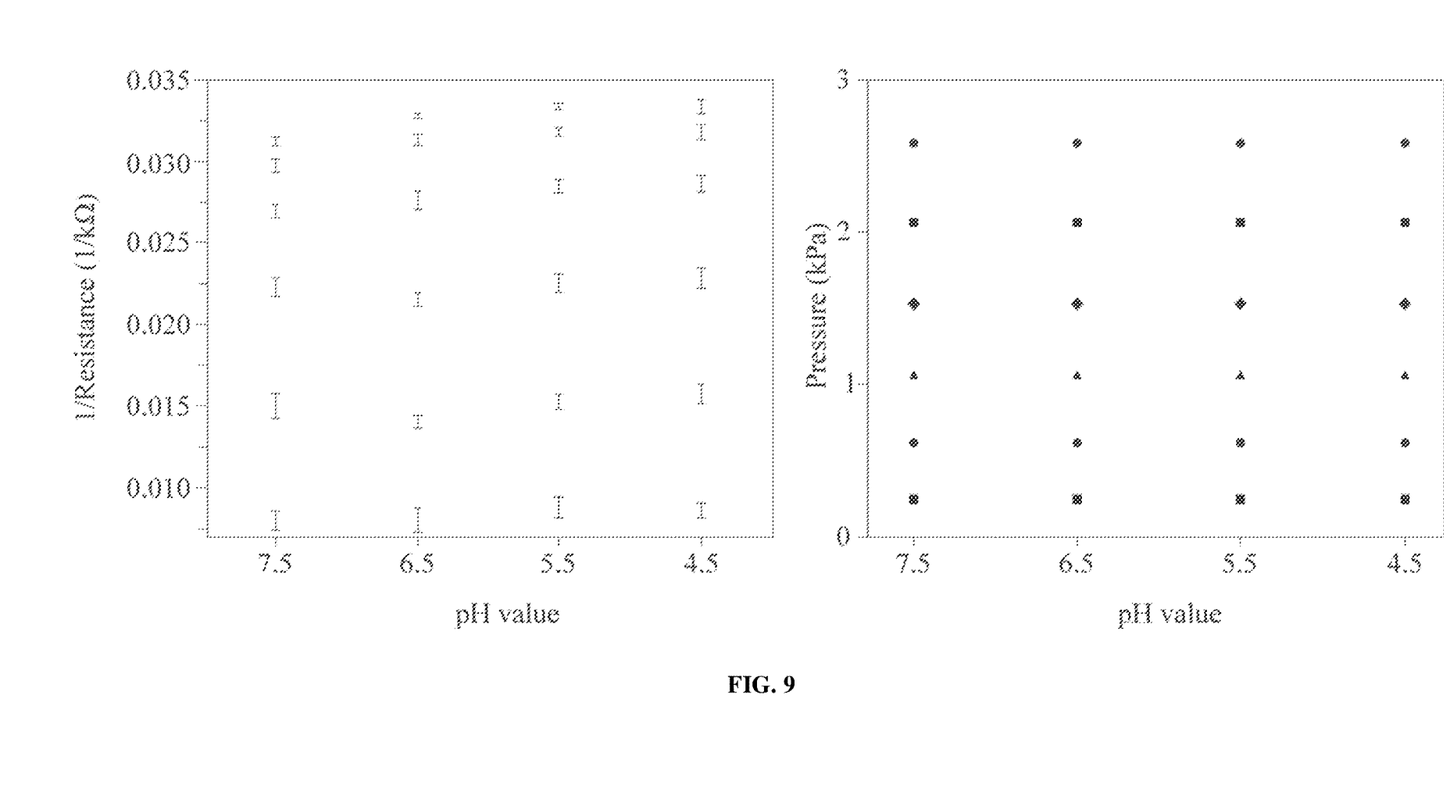
FIG. 9 is a diagram illustrating the measurement difference of the pH value and the calibration thereof according to an embodiment of the invention.

FIG. 9 is a diagram illustrating the measurement difference of the pH value and the calibration thereof according to an embodiment of the invention. In FIGS. 9 and 12, the monitored results are affected by the ion concentration more significantly than by the pH value, and further, the difference of the monitor results caused by the pH value appears only under extremely high pressure. However, the effect caused by the pH value were still calibrated according to the embodiment of the invention, and the resistance distributions of the smaller pH value was found to have the similar tendency to the resistance distributions of the higher ion concentration. Therefore, the resistance value of the sweat advanced to the first pair of the sub-electrodes 116a, 116b by using the Arduino micro-control system was then measured. Further, the calculation of the equivalent circuit 335 as above was used to eliminate the effect caused by the pH value and the calibration curve of the corresponding pH value was then directly introduced.

Figure 10:
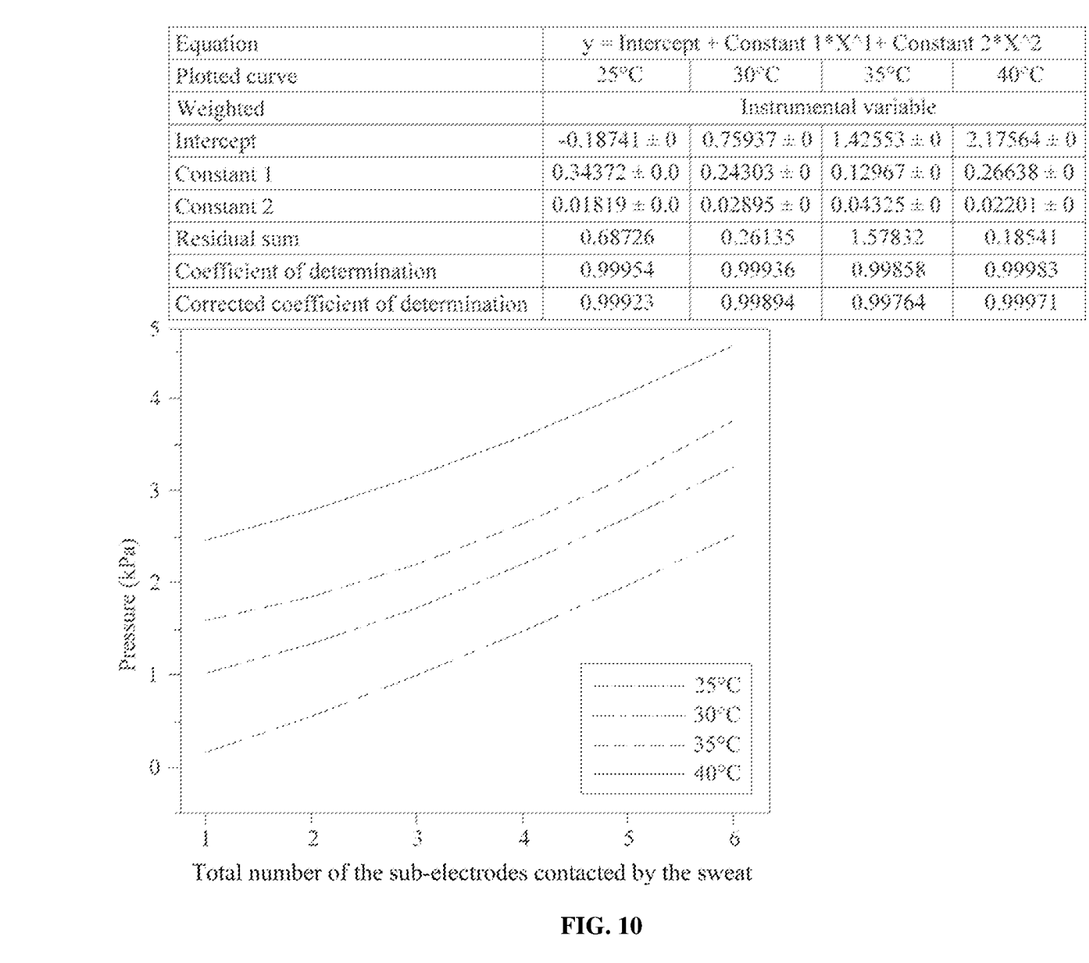
FIG. 10 is a diagram illustrating the pressure under different temperatures according to an embodiment of the invention.
Figure 11:
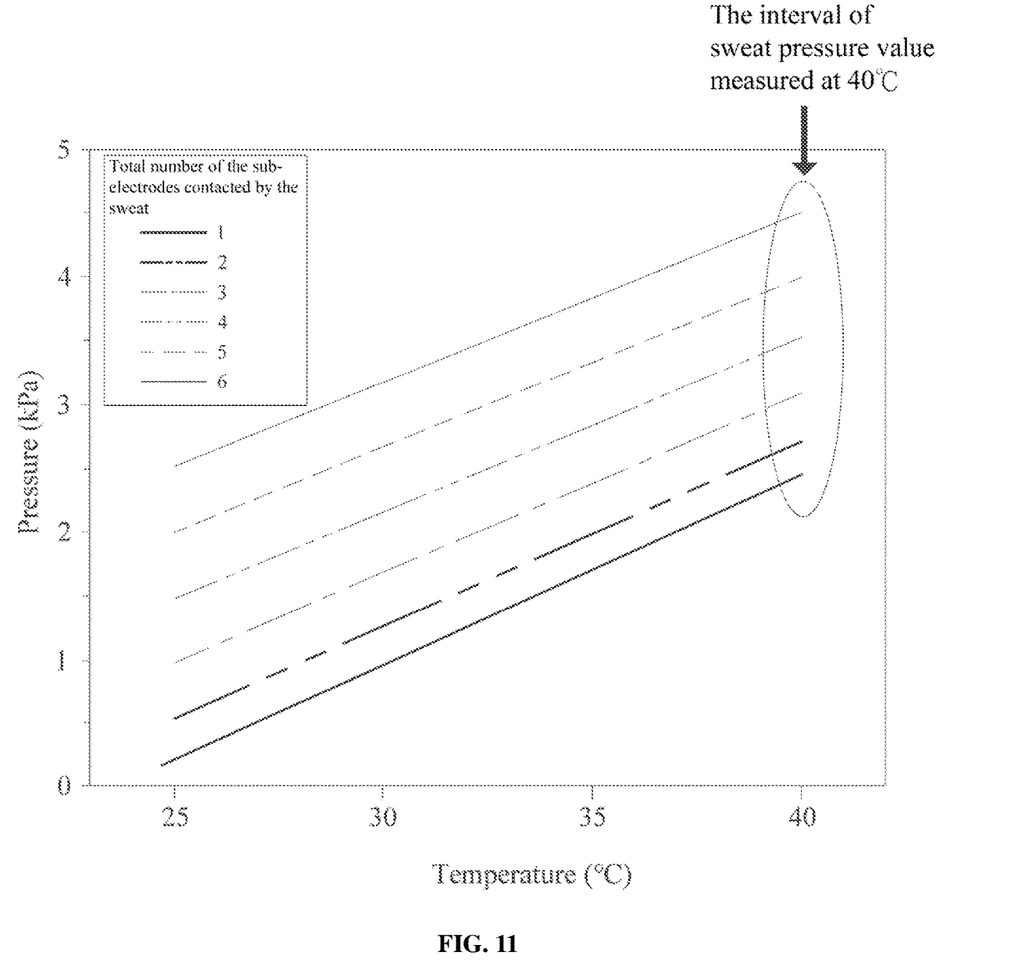
FIG. 11 is a diagram illustrating the pressure under different temperatures calibrated by the temperature calibration curves in FIG. 10 according to the embodiment of the invention.

FIG. 10 is a diagram illustrating the pressure under different temperatures according to an embodiment of the invention, and FIG. 11 is a diagram illustrating the pressure under different temperatures calibrated by the temperature calibration curves in FIG. 10 according to the embodiment of the invention. The impedance-type chip according to the embodiment of the invention is supposed to be attached to the skin of the subject, so the sweat pressure is inevitably affected by the body temperature or the environmental temperature. In FIGS. 10-11, the temperature calibration curve according to the embodiment of the invention was introduced to calibrate the sweat pressure value in accordance with the temperature measured by using the temperature sensor 220.

It should be mentioned that the sweating is happened only when the sweat generation rate exceeds the sweat absorption rate by the skin because the sweat glands on the skin have the function of absorbing the sweat. The averaged sweat reabsorption rate of a normal person is about 10 mL/min-m², and 0-50 mL/min-m² when exercising, so the sweat volume in the impedance-type chip 100 according to the embodiments of the invention is adjustable, continuously measurable and traceable.

The embodiments of the invention are disclosed herein. However, any person skilled in the art should understand that the embodiments are only used to describe the invention and are not intended to limit the scope of the patent rights claimed by the invention. Any changes or substitutions equivalent to the embodiments of the invention should be interpreted as being covered within the spirit or scope of the invention. Therefore, the protection scope of the invention shall be subject to the scope defined by the claims as below.

What is claimed is:

1. An impedance-type chip for real-time sensing sweat pressure to monitor and record a physiological state of a subject, the chip comprising:
   a substrate;
   a pair of comb-shaped electrodes comprising plural pairs of oppositely-disposed sub-electrodes, on the substrate, to provide different impedance values;
   a first double-layered junction plate disposed on the substrate and the comb-shaped electrodes;
   a microfluidic channel plate disposed on the first double-layered junction plate;
   a second double-layered junction plate disposed on the microfluidic channel plate, wherein the first double-layered junction plate, the microfluidic channel plate, and the second double-layered junction plate define a microfluidic channel with a sweat inflow hole, and a cavity connected with the microfluidic channel, wherein the microfluidic channel overlaps on the comb-shaped electrodes; and
   a sealing plate disposed on the second double-layered junction plate to seal the microfluidic channel and the cavity, wherein the sealing plate comprises a sweat inflow hole disposed on the sweat inflow hole of the microfluidic channel.

2. The chip of claim 1, wherein each pair of the oppositely-disposed sub-electrodes comprises a gap of 1-1.4 mm.

3. The chip of claim 1, further comprising a sweat monitor configured to measure a sweat resistance value between the comb-shaped electrodes and a total number of the sub-electrodes contacted by sweat.

4. The chip of claim 1, further comprising a temperature sensor configured to measure a body temperature of the subject.

5. The chip of claim 1, further comprising a communicating circuit configured to output a sweat resistance value, the total number of the sub-electrodes contacted by the sweat, and a body temperature.

6. A micro-control system for controlling the impedance-type chip of claim 5, the micro-control system comprising:
   a pulsed voltage output module configured to regularly output a pulsed voltage to the pair of the comb-shaped electrodes in real time;
   a signal correction module configured to output an inverse pulsed voltage, opposite to the pulsed voltage, to the pair of the comb-shaped electrodes in real time;
   an equivalent resistance and correction module configured to receive the sweat resistance value, the total number of the sub-electrodes contacted by the sweat and the body temperature of the subject output by the communicating circuit, and output a calibrated resistance value and the body temperature; and
   a sweat pressure conversion module configured to receive and convert the calibrated resistance value and the body temperature to a sweat pressure value.

7. The micro-control system of claim 6, further comprising a bluetooth module configured to receive and output the sweat pressure value to an external device.

8. The micro-control system of claim 6, wherein the equivalent resistance and correction module further comprises an equivalent circuit configured to correct an effect to the sweat resistance value caused by a sweat ion concentration and a sweat pH value via a normalized curve based on the sweat resistance value and the total number of sub-electrodes contacted by the sweat, as well as calculate the calibrated resistance value.

* * * * *